United States Patent
Fritz et al.

(10) Patent No.: US 8,451,447 B2
(45) Date of Patent: *May 28, 2013

(54) PHOTOACOUSTIC SENSOR

(75) Inventors: Bernard S. Fritz, Eagan, MN (US); Matthew S. Marcus, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/312,368

(22) Filed: Dec. 6, 2011

(65) Prior Publication Data

US 2012/0075618 A1    Mar. 29, 2012

Related U.S. Application Data

(63) Continuation of application No. 12/195,531, filed on Aug. 21, 2008, now Pat. No. 8,085,403.

(51) Int. Cl.
*G01N 21/00* (2006.01)

(52) U.S. Cl.
USPC .......................................................... 356/437

(58) Field of Classification Search
None
See application file for complete search history.

(56) References Cited

U.S. PATENT DOCUMENTS

| | | | |
|---|---|---|---|
| 4,457,162 A | 7/1984 | Rush et al. | |
| 5,933,245 A | 8/1999 | Wood et al. | |
| 6,618,148 B1 | 9/2003 | Pilgrim et al. | |
| 7,208,737 B2 * | 4/2007 | Kauppinen | 250/339.13 |
| 8,085,403 B2 * | 12/2011 | Fritz et al. | 356/437 |
| 2007/0221867 A1 | 9/2007 | Beeson et al. | |
| 2011/0052447 A1 * | 3/2011 | Roy et al. | 422/82.05 |

FOREIGN PATENT DOCUMENTS

| | | |
|---|---|---|
| EP | 1111367 A2 | 6/2001 |
| EP | 1857789 A2 | 11/2007 |
| JP | 2006323410 | 11/2006 |

OTHER PUBLICATIONS

"U.S. Appl. No. 12/195,531, Response filed Aug. 11, 2011 to Non Final Office Action mailed May 13, 2011", 8 pgs.
"U.S. Appl. No. 12/195,531, Non Final Office Action mailed May 13, 2011", 4 pgs.
"U.S. Appl. No. 12/195,531, Notice of Allowance mailed Aug. 29, 2011", 6 pgs.
"European Application Serial No. 09168210.4, Office Action mailed Dec. 28, 2009", 6 pgs.
"European Application Serial No. 09168210.4, Search Report mailed Dec. 8, 2009", 5 pgs.

(Continued)

*Primary Examiner* — Robert R Raevis
(74) *Attorney, Agent, or Firm* — Schwegman, Lundberg & Woessner, P.A.

(57) ABSTRACT

Embodiments of the apparatus, systems, and methods relate to a photoacoustic sensor includes an excitation source, a modulator, a quantum dot filter, an interferometer, a gas chamber, and a microphone. The excitation source generates a monochromatic light. The modulator intensity modulates the monochromatic light at a first modulation frequency. The quantum dot filter down converts the modulated monochromatic light into a broadband spectrum of infrared light. The interferometer further intensity modulates the broadband spectrum such that the at least one wavelength component of the broadband spectrum is further intensity modulated at a second modulation frequency. The gas chamber stores a sample gas and receives the plurality of modulated wavelength components. The microphone detects pressure changes within the gas chamber to produce an acoustic signal, which can be used to analyze properties of the sample gas.

20 Claims, 4 Drawing Sheets

OTHER PUBLICATIONS

Rockley, M. G, et al., "Fourier-transformed infrared photoacoustic spectroscopy, the technique and its application", Proc. IEEE UltrasonicSymposium, (Nov. 5, 1980), 649-651.

Schilt, S., et al., "Continuous and simultaneous multigas monitoring using a highly sensitive and selective photoacoustic sensor", Proc. CLEO 2005, (2005), 1215-1217.

* cited by examiner

PHOTOACOUSTIC SENSOR

RELATED APPLICATIONS

This application is a continuation of U.S. patent application Ser. No. 12/195,531, filed Aug. 21, 2008, which application is incorporated herein by reference in its entirety.

TECHNICAL FIELD

Various embodiments described herein relate generally to a sensor, and more particularly to a photoacoustic sensor.

BACKGROUND

Photoacoustic measurement is based on the tendency of molecules in a gas, when exposed to certain wavelengths of radiant energy (e.g. infrared light), to absorb the energy and reach higher levels of molecular vibration and rotation, thereby reaching a higher temperature and pressure within a measurement cell. When the radiant energy striking a gas is amplitude or intensity modulated at a known frequency, the resulting fluctuations in energy available for absorption produce corresponding temperature and pressure fluctuations in the gas, which can be measured as an acoustic signal. The amplitude of the acoustic signal is proportional to the intensity of the radiation and the concentration value of the absorbing gas. Such devices are well suited for measuring small concentration values of gases (i.e., in the parts-per-billion range).

However, it is a challenging task to analyze a large range of different analytes efficiently and economically.

BRIEF DESCRIPTION OF THE DRAWINGS

Some embodiments are illustrated by way of examples, and not by way of limitation, in the figures of the accompanying drawings in which.

DETAILED DESCRIPTION

In the following detailed description of embodiments of the subject matter, reference is made to the accompanying drawings, which form a part hereof, and in which is shown by way of illustration some embodiments in which the subject matter may be practiced.

Various embodiments provide a photoacoustic sensor, which includes an excitation source, a modulator, a quantum dot filter, an interferometer, a gas chamber, and a microphone. The excitation source may generate monochromatic light. The modulator may intensity modulate the monochromatic light at a first modulation frequency. The quantum dot filter may down-convert the modulated monochromatic light into a broadband spectrum of infrared light. The interferometer may further intensity modulate the broadband spectrum such that at least one of the plurality of wavelength components of the broadband spectrum is further intensity modulated at a second modulation frequency, which is, for example, related to the distinct wavelength of that wavelength component and the scanning speed of the interferometer. Thus, the resultant modulation frequency of that wavelength component of the broadband spectrum emitted from the interferometer is determined, for example, by the first modulation frequency, the distinct wavelength of that wavelength component, and the scanning speed of the interferometer. The gas chamber may store a sample gas and receive the resultant broadband spectrum emitted from the interferometer. The microphone may detect pressure changes within the gas chamber to produce an acoustic signal, which can be used to identify and analyze one or more gases contained in the gas chamber.

In the embodiments, the photoacoustic sensor, commonly called Fourier Transform Photoacoustic (FTPA) sensor, is used to generate a broadband light source, in which wavelength components in the broadband light source are intensity modulated at different resultant frequencies related to the first modulation frequency, the wavelength of the particular wavelength component, and the scanning speed of the interferometer, for example.

Figure 1:
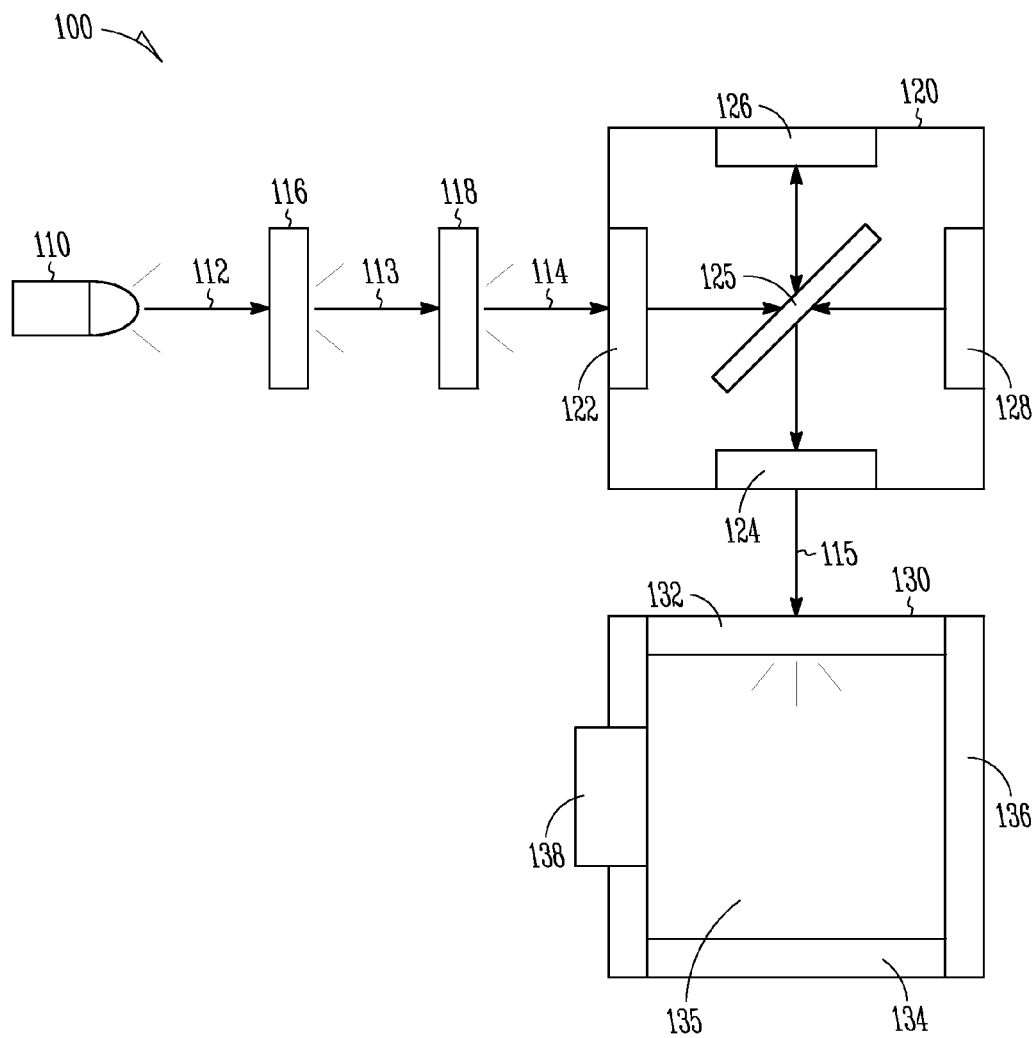
FIG. 1 is a diagram illustrating a photoacoustic sensor according to an example embodiment.

FIG. 1 shows a photoacoustic sensor 100 according to an example embodiment. Photoacoustic sensor 100 comprises an excitation source 110, a modulator 116, a quantum dot filter 118, an interferometer 120, and a gas chamber 130.

In some embodiments, the excitation source 110 may be a laser or an LED, which may generate a monochromatic light 112. The modulator 116 may intensity (or amplitude) modulate the monochromatic light 112 at a first modulation frequency f(1) to create a beam of intensity modulated monochromatic light 113. In some embodiments, the first modulation frequency f(1) is in a range of 0 kHz and 10 kHz. In an alternative embodiment, a power supply of the monochromatic light 112 can be used to modulate the monochromatic light 112.

In some embodiments, the quantum dot filter 118 may down-convert the high-energy intensity modulated monochromatic light 113 into a low-energy broadband spectrum 114 of infrared light, which includes a plurality of wavelength components with distinct wavelengths. Therefore, the resulting broadband spectrum 114 of down-converted light from the quantum dot filter 118 is also modulated at the first modulation frequency f(1) and is output to the interferometer 120.

In an embodiment, the quantum dot filter 118 is selected such that the distinct wavelength λ of wavelength components of the broadband spectrum of infrared light 114 emitted by the quantum dot filter 118 corresponds to an energy absorption band of one of a plurality of target sample gases. Generally, when assembling the photoacoustic sensor 130, it will be known what particular gases the sensor will be used to detect. Therefore, in selecting the quantum dot filter 118, one only needs to determine unique absorption bands of the particular gases, i.e. absorption bands that are not shared with other gases, and then select a quantum dot filter 118 with similar corresponding emission peaks. In order to detect multiple gases, an interchangeable array of quantum dot filters (or substrates) may be used, in which each quantum dot filter emits a different group of wavelengths corresponding to the absorption peaks of a different group of gases. As is known, the emission peaks of a quantum dot filter are predominately determined by the sizes and compositions of the quantum dots.

In some embodiments, the interferometer 120 may further intensity modulate the broadband spectrum 114 of infrared light, and then output the further intensity modulated broadband spectrum 115 of infrared light to the gas chamber 130.

As shown in FIG. 1, for example, a Michelson interferometer 120 is used to further intensity modulate the broadband spectrum 114 of infrared light. The Michelson interferometer 120 may include, for example, an input port 122, an output port 124, a beamsplitter (e.g., semi-transparent mirror) 125, a scanning minor 126 and another minor 128. In an embodiment, the Michelson interferometer 120 may further intensity modulate each wavelength component of the broadband spectrum 114 of infrared light at a distinct second modulation frequency $f(2\lambda)$, which is determined by both distinct wavelength $\lambda$ of each wavelength component and the scanning speed v of the Michelson interferometer 120. Thus, the resultant broadband spectrum 115 of infrared light exiting from the output port 124 of the Michelson interferometer 120 is intensity modulated with frequency components at frequencies $f(a)=f(1)+f(2\lambda)$ and $f(b)=f(1)-f(2\lambda)$, in which frequency $f(2\lambda)$ is a function of a scanning speed v of the Michelson interferometer 120 and a distinct wavelength $\lambda$ of each distinct wavelength component of the broadband spectrum 114 of infrared light, herein $f(2\lambda)=2v/\lambda$.

Although a Michelson interferometer is illustrated in this embodiment, other types of interferometers, for example, a lamellar grating, can also be used to further intensity modulate each distinct wavelength component of the broadband spectrum 114 of infrared light at a distinct frequency.

In some embodiments, the gas chamber 130 includes a light transparent wall 132, a gas permeable wall 134 to introduce one or more gases, a measurement volume 135 to store the one or more gases, an outer wall 136, and a microphone 138. The gas chamber 130 receives the broadband spectrum 115 of infrared light through the light transparent wall 132, in which the broadband spectrum 115 has a plurality of distinct wavelength components modulated at distinct frequencies. The microphone 138, which is coupled to the gas chamber 130, detects pressure changes within the gas chamber 130 to produce an acoustic signal 139, which is representative of the properties of a sample gas stored in the gas chamber to identify the one or more gases and analyze their properties.

The microphone 138 is sensitive to acoustic signals, and is coupled to detect pressure changes within the gas chamber 130. Pressure changes within gas chamber 130 are caused by gases within the gas chamber 130 absorbing the radiant energy of one or more of the distinct component wavelength 115 and changing temperature as a result. The temperature fluctuations in the gas track modulation frequencies $f(2\lambda)$ of the distinct wavelength components 115. Within chamber 130, pressure fluctuations that accompany the temperature fluctuations are detected by the microphone 138. Any suitable acoustic transducer may be used as the microphone 138. In an embodiment, the microphone 138 may comprise an electronic microphone. In an alternative embodiment, microphone 138 may comprise a piezoelectric material.

The outer wall 136 of the gas chamber 130 may be constructed of any suitable material. In an embodiment, the outer wall 136 may comprise a metal, such as aluminum. In an alternative embodiment, the outer wall 136 may comprise a plastic, or polymer, such as methacrylate.

The gas permeable wall 134 may be covered by a porous membrane formed of paper, a porous metal, or a gas permeable polymer. Thus, after photoacoustic sensor 100 is located for several minutes within a given environment, the gas mixture within the gas chamber 130 will substantially match the gas mixture of the surrounding environment. In an alternative embodiment, the wall 134 may also be a valve type of structure that would open and introduce the sample gas into the gas chamber 130 and then close to make the measurement.

Figure 2:
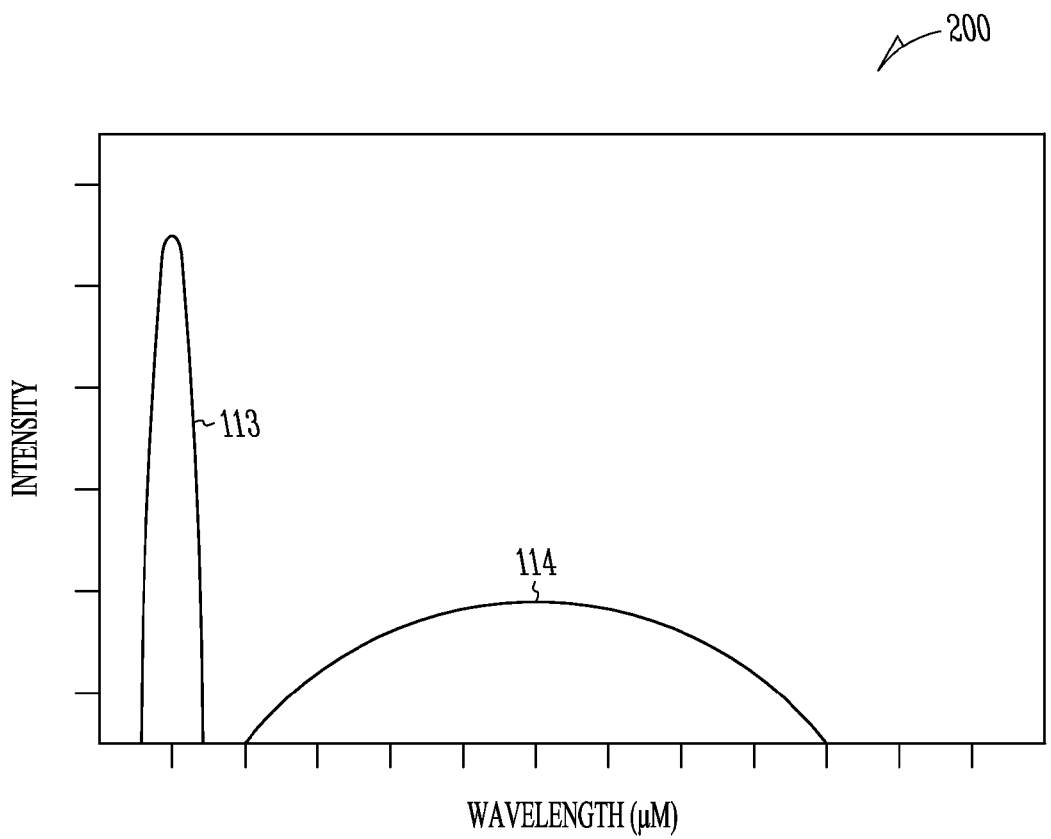
FIG. 2 is a graph diagram illustrating wavelength and intensity of light used by a photoacoustic sensor according to an example embodiment.

FIG. 2 is a graph 200 illustrating wavelength and intensity of light used by a photoacoustic sensor 100 according to an example embodiment. Graph 200 shows, in an example embodiment, that the quantum dot filter 118 down-converts the high-energy intensity modulated monochromatic light 113 into a low-energy broadband spectrum 114 of infrared light (shown on the x-axis, in microns), which includes a plurality of wavelength components with distinct wavelength. Graph 200 also shows that the spectrum 114 emitted by the quantum dot filter 118 is within a broad range of wavelengths in the infrared band, and is of a longer wavelength than the modulated monochromatic light 113.

Figure 3:
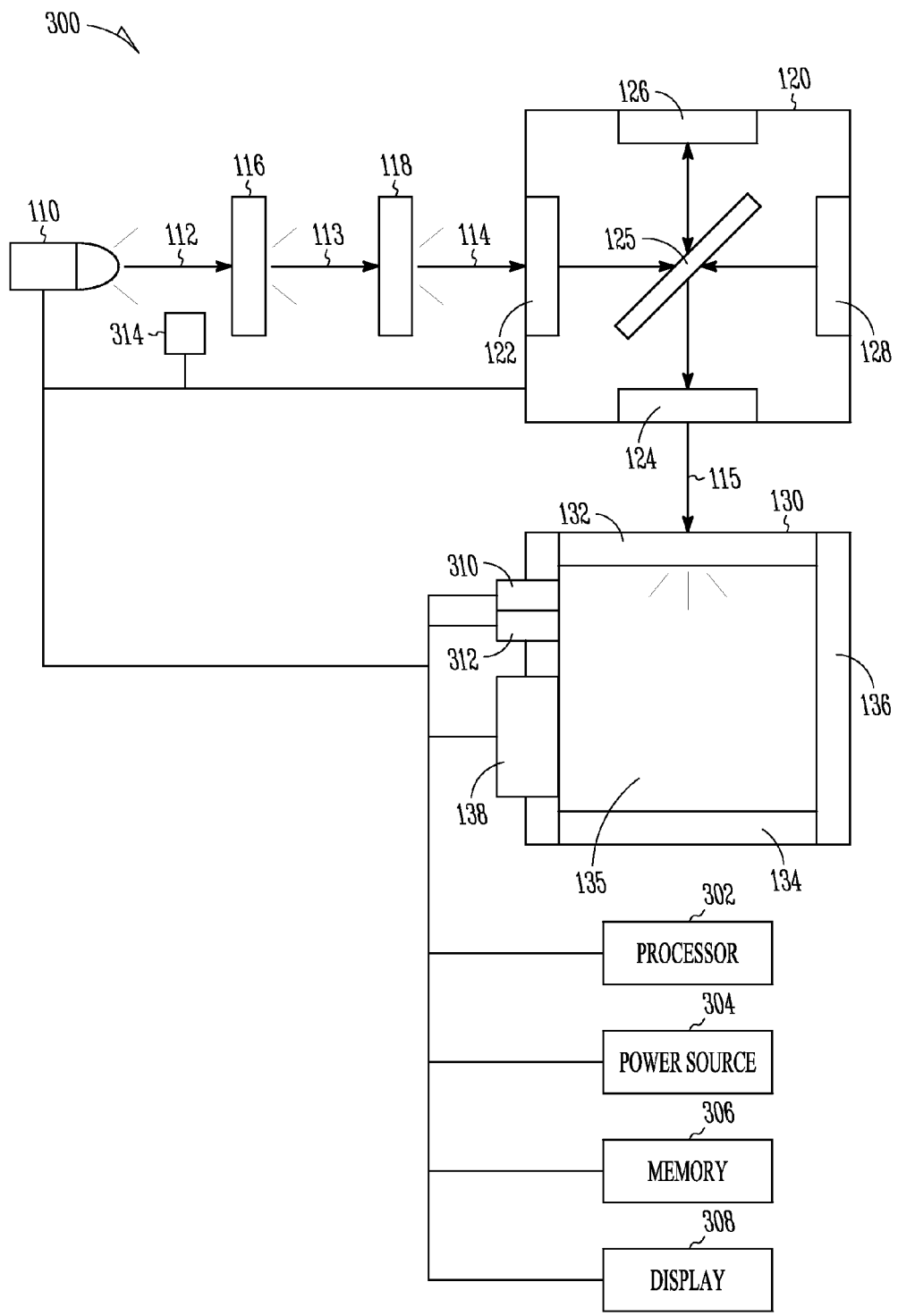
FIG. 3 is a diagram illustrating a photoacoustic gas sensing system according to an example embodiment.

FIG. 3 is a diagram illustrating a photoacoustic gas sensing system 300 according to an example embodiment. The photoacoustic gas sensing system 300 comprises an excitation source 110, a modulator 116, a quantum dot filter 118, an interferometer 120, a gas chamber 130 (which has a light transparent wall 132, a gas permeable wall 134, an outer wall 136, and a microphone 138), a temperature sensor 310, a pressure sensor 312, a photodiode 314, a processor 302, a power source 304, a memory 306, and a display 308. Elements 110, 116, 118, 120, 130, 132, 134, 136, and 138 may be identical or similar to the elements described in FIG. 1.

The temperature sensor 310 is coupled to the microphone 138. The temperature sensor 310 measures the temperature of the microphone 138 in order to generate a correction signal to compensate for temperature induced changes in sensitivity of the microphone 118. Any suitable temperature measurement device may be used for this purpose. In an embodiment, the temperature sensor 310 may comprise a thermocouple.

The pressure sensor 312 is coupled to the gas chamber 130. Pressure sensor 312 measures the atmospheric pressure of the gas chamber 130 in order to generate a pressure correction signal. The pressure sensor 312 may be used to compensate for variations in the environment surrounding photoacoustic sensor 100. For example, the pressure sensor 312 may be used to compensate for changes in barometric pressure caused by a change in altitude or weather conditions. Any suitable pressure measurement device may be used for this purpose.

The photodiode 314 is located between the excitation source 110 and the intensity modulator 116. Photodiode 314 is positioned to measure the intensity of the monochromatic light 112 emitted by the excitation source 110, and may be used for the purpose of calibrating the photoacoustic gas sensing system 300.

The processor 302 receives signals related to pressure changes within the gas chamber 130. The processor 302 is electrically coupled to the excitation source 110 and the microphone 138. The processor 302 includes circuitry for controlling the modulation of the excitation source 110, as well as circuitry for receiving and processing signals from the microphone 138, the temperature sensor 310, the pressure sensor 312, and the photodiode 314. The processor 302 performs calculations on the signals to identify the one or more gases within the gas chamber 130 and a concentration corresponding to each of those gases. In an embodiment, the processor 302 may comprise a microcontroller.

The memory 306 is used by the processor circuitry during operation, and may include random access memory (RAM), one or more hard drives, and/or one or more drives that handle removable media.

The display 308 indicates the presence and respective concentration values of the particular gases within the gas chamber 130. The display 308 may comprise any suitable output device, including a video terminal, LED indicator, analog gauge, printer, or other peripheral device. Generally, the display 308 indicates concentration measures of particular gases in terms of parts per million (ppm). The display 308 may also be used to indicate the modulation frequency of excitation source 110. In an embodiment, the display 308 indicates the concentration value corrected for ambient temperature and pressure. In an alternative embodiment, the display 308 comprises an indicator lamp or LED that illuminates when the concentration of a particular gas reaches a predetermined level.

The power source 304 provides power to the excitation source 110, the modulator 116, the microphone 138, the temperature sensor 310, the pressure sensor 312, the processor 302, the memory 306, and the display 308. In an embodiment, the system 300 is portable, and the power source 304 may comprise a battery, such as a rechargeable lithium-ion battery. In an alternative embodiment, the power source 304 may comprise an alternating current (AC) adaptor.

Figure 4:
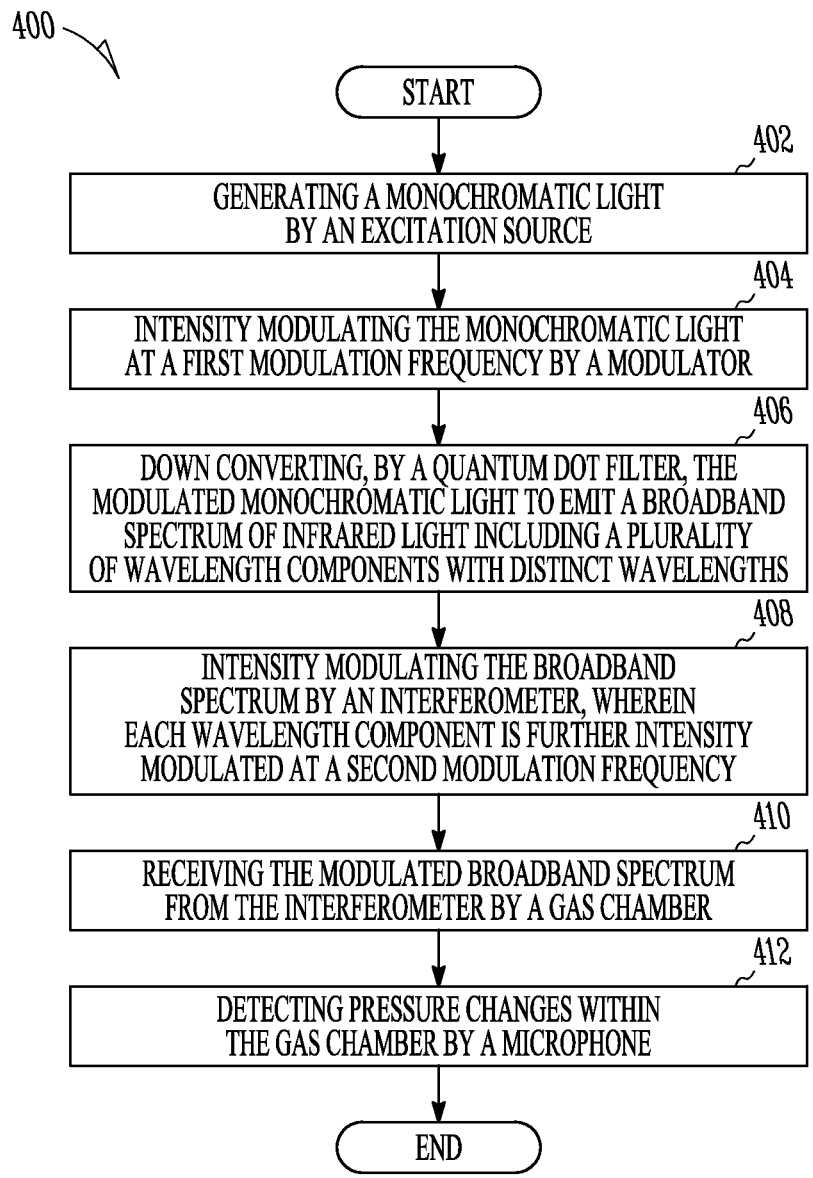
FIG. 4 is a flow diagram illustrating a method of detecting gas by a photoacoustic sensor according to an example embodiment.

FIG. 4 is a flow diagram 400 illustrating a method of detecting gas by a photoacoustic sensor 100 as shown in FIG. 1 according to an example embodiment.

In 402, the excitation source 110, for example a laser device or LED, generates a monochromatic light 112, for example a laser.

In 404, the modulator 116 intensity modulates the monochromatic light 112 at a first modulation frequency f(1) to generate a modulated monochromatic light 113. In an embodiment, the first modulation frequency f(1) is, for example, in a range of kHz and 10 kHz.

In 406, the quantum dot filter 118 down-converts the modulated monochromatic light 113 to a broadband spectrum 114 of infrared light, which includes a plurality of wavelength components with distinct wavelengths. Therefore, the broadband spectrum 114 of the down-converted light emitted from the quantum dot filter 118 is also modulated at the first modulation frequency f(1) and is output to the input port 122 of the interferometer 120.

In 408, the interferometer 120 further intensity modulates the input broadband spectrum 114 of infrared light at a second frequency f(2λ), and then output the resultant intensity modulated broadband spectrum 115 of infrared light through the output port 124 of the interferometer 120.

By the virtue of the further intensity modulation applied by the interferometer 120 (such as a Michelson interferometer), each wavelength component of the broadband spectrum 114 of infrared light is further intensity modulated at a second modulation frequency f(2λ), which is a function of a scanning speed v of the interferometer 120 and a distinct wavelength λ of each wavelength component. For example, with a Michelson interferometer 120 used, the second modulation frequency f(2λ) of each wavelength component of the broadband spectrum 114 of infrared light may be expressed in the formula: $f(2\lambda)=2v/\lambda$. Then, each wavelength component of the resultant broadband spectrum 115 of infrared light is finally intensity modulated with frequency components at frequencies $f(a)=f(1)+f(2\lambda)$ and $f(b)=f(1)-f(2\lambda)$.

In 410, the gas chamber 130 receives the resultant modulated broadband spectrum 115 of infrared light emitted from the interferometer 120.

In 412, the microphone 138 detects pressure changes within the gas chamber 130 to produce an acoustic signal corresponding to one or more energy absorption of one or more gases contained in the gas chamber. These pressure changes will occur at the resultant frequencies of each wavelength component of the resultant broadband spectrum 115 of infrared light, and will vary in intensity according to the concentration of the one or more gases. Pressure changes are detected and converted to an electrical signal by the microphone 138. A processor may then be used to perform calculations on the electrical signal produced by the microphone 138, which allows for the determination of the presence and concentration of one or more gases. The concentrations of the one or more gases may be displayed, or may be used to trigger an alarm if greater than a predetermined level.

In the foregoing Detailed Description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate preferred embodiment.

The invention claimed is:

1. A photoacoustic sensor comprising:
a quantum dot filter to down convert an input monochromatic light into a broadband spectrum of infrared light, which includes a plurality of wavelength components with distinct wavelengths; and
an interferometer to intensity modulate the broadband spectrum, wherein at least one of the plurality of wavelength components is intensity modulated at a modulation frequency related to a scanning speed of the interferometer and a distinct wavelength of the wavelength component to produce an output resultant broadband spectrum of infrared light.

2. The photoacoustic sensor of claim 1, further comprising:
a gas chamber to store a sample gas and to receive the output resultant broadband spectrum of infrared light.

3. The photoacoustic sensor of claim 2, further comprising:
a microphone coupled to the gas chamber to detect pressure changes within the gas chamber to produce an acoustic signal representative of properties of the sample gas.

4. The photoacoustic sensor of claim 2, wherein the gas chamber comprises at least one gas permeable wall through which a sample gas may be introduced.

5. The photoacoustic sensor of claim 1, wherein the modulation frequency is directly proportional to the interferometer scanning speed and is inversely proportional to the distinct wavelength of the at least one wavelength component.

6. The photoacoustic sensor of claim 1, further comprising:
an excitation source to generate a monochromatic light;
a modulator to intensity modulate the monochromatic light at a first modulation frequency into the input monochromatic light.

7. The photoacoustic sensor of claim 6, wherein the output resultant broadband spectrum of infrared light is modulated at a resultant frequency of the first modulation frequency and the modulation frequency.

8. A method of detecting gas by a photoacoustic sensor, comprising:
down-converting an input monochromatic light to emit a broadband spectrum of infrared light, which includes a plurality of wavelength components with distinct wavelengths; and
intensity modulating the broadband spectrum of infrared light by an interferometer, wherein at least one of the plurality of wavelength components is intensity modulated at a modulation frequency, which is related to a scanning speed of the interferometer and a distinct wavelength of that wavelength component, to produce an output broadband spectrum.

9. The method of claim 8, further comprising:
receiving the output broadband spectrum within a gas chamber; and
detecting pressure changes within the gas chamber to produce one or more acoustic signals corresponding to one or more energy absorption of one or more gases within in the gas chamber.

10. The method of claim 8, wherein the modulation frequency is directly proportional to the interferometer scanning speed and is inversely proportional to the distinct wavelength of the at least one wavelength component.

11. The method of claim 8, further comprising:
generating a monochromatic light from an excitation source;
intensity modulating the monochromatic light at a first modulation frequency to produce the input monochromatic light.

12. The method of claim 11, wherein the first modulation frequency is in a range of 0-10 kilohertz.

13. The method of claim 11, wherein the output broadband spectrum of infrared light is modulated at a resultant frequency of the first modulation frequency and the modulation frequency.

14. The method of claim 8, further comprising:
selecting the quantum dot filter such that the distinct wavelength of the at least one wavelength component of the broadband spectrum of infrared light emitted by the quantum dot filter corresponds to an energy absorption band of one of a plurality of target sample gases.

15. A photoacoustic gas sensing system comprising:
an interferometer to intensity modulate a broadband spectrum, wherein each wavelength component is intensity modulated at a modulation frequency, which is a function of a scanning speed of the interferometer and a distinct wavelength of each wavelength component, to produce a resultant broadband spectrum of infrared light; and
a gas chamber to store a sample gas and to receive the resultant broadband spectrum of infrared light.

16. The photoacoustic gas sensing system of claim 15, wherein the modulation frequency is directly proportional to the interferometer scanning speed and is inversely proportional to the distinct wavelength of the at least one wavelength component.

17. The photoacoustic gas sensing system of claim 15, further comprising:
an intensity modulated excitation source to produce the broadband infrared spectrum.

18. The photoacoustic gas sensing system of claim 15, further comprising:
a microphone positioned onto the gas chamber to detect pressure changes within the gas chamber to produce an acoustic signal representative of properties of the sample gas.

19. The photoacoustic gas sensing system of claim 18, further comprising:
a processor electrically coupled to the microphone to receive the acoustic signal.

20. The photoacoustic gas sensing system of claim 19, wherein the processor performs calculations on the acoustic signal to identify one or more gases contained in the gas chamber and a concentration related to the one or more gases.

* * * * *